(12) United States Patent
Han

(10) Patent No.: US 10,819,711 B2
(45) Date of Patent: Oct. 27, 2020

(54) DATA ACCESS METHOD, USER EQUIPMENT AND SERVER

(71) Applicant: BOE TECHNOLOGY GROUP CO., LTD., Beijing (CN)

(72) Inventor: Litong Han, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 206 days.

(21) Appl. No.: 16/028,828

(22) Filed: Jul. 6, 2018

(65) Prior Publication Data
US 2019/0068607 A1    Feb. 28, 2019

(30) Foreign Application Priority Data

Aug. 22, 2017  (CN) .......................... 2017 1 0726243

(51) Int. Cl.
*H04L 29/06* (2006.01)
*H04W 12/06* (2009.01)
*G16H 10/60* (2018.01)
*H04W 4/80* (2018.01)
*H04W 12/00* (2009.01)

(52) U.S. Cl.
CPC .......... *H04L 63/102* (2013.01); *G16H 10/60* (2018.01); *H04L 63/08* (2013.01); *H04L 63/0853* (2013.01); *H04L 63/105* (2013.01); *H04W 12/06* (2013.01); *H04W 4/80* (2018.02); *H04W 12/00409* (2019.01)

(58) Field of Classification Search
CPC ... H04L 63/102; H04L 63/08; H04L 63/0853; H04L 63/105; G16H 10/60; H04W 12/06; H04W 4/80; H04W 12/00409

USPC .......................................................... 726/7
See application file for complete search history.

(56) References Cited

U.S. PATENT DOCUMENTS 8,887,212 B2 * 11/2014 Dua ................. H04N 21/42206
725/81
2008/0081608 A1 * 4/2008 Findikli .............. H04M 1/7253
455/425

(Continued)

FOREIGN PATENT DOCUMENTS

CN      103298144 A     9/2013
CN      103441997 A    12/2013
(Continued)

OTHER PUBLICATIONS

CN103298144A, English Abstract and U.S. Equivalent U.S. Pub. No. 2015/0009016.

(Continued)

*Primary Examiner* — Michael S McNally
(74) *Attorney, Agent, or Firm* — Brooks Kushman P.C.

(57) ABSTRACT

A data access method, a UE and a server are provided. The data access method includes: acquiring, by the UE, authentication data from an NFC circuit; transmitting, by the UE, the authentication data to a second NFC circuit of the server for authentication via a network connection between the UE and the server; and in the case that the UE has been authenticated successfully, transmitting, by the UE, a data access request to the server via the network connection, and accessing to-be-accessed data that corresponds to the data access request and is transmitted by the server.

16 Claims, 2 Drawing Sheets

(56) References Cited

U.S. PATENT DOCUMENTS

| | | | | |
|---|---|---|---|---|
| 2013/0145420 | A1* | 6/2013 | Ting | H04L 63/08 726/1 |
| 2014/0020073 | A1* | 1/2014 | Ronda | G06F 21/31 726/7 |
| 2014/0067682 | A1* | 3/2014 | Song | H04L 63/0853 705/44 |
| 2014/0298434 | A1* | 10/2014 | Prchal | H04W 12/0609 726/7 |
| 2014/0304795 | A1 | 10/2014 | Bruno et al. | |
| 2015/0009016 | A1* | 1/2015 | Dai | H04W 48/16 340/10.1 |
| 2015/0067793 | A1* | 3/2015 | Robison, Jr. | H04L 63/0838 726/5 |
| 2015/0119000 | A1 | 4/2015 | Miao et al. | |
| 2016/0217454 | A1* | 7/2016 | Killoran, Jr. | G06Q 20/3278 |
| 2016/0381011 | A1* | 12/2016 | Mu | H04W 12/0608 713/169 |
| 2017/0195322 | A1* | 7/2017 | Cho | G07C 9/27 |
| 2017/0311160 | A1 | 10/2017 | Feng et al. | |

FOREIGN PATENT DOCUMENTS

| | | |
|---|---|---|
| CN | 103796203 A | 5/2014 |
| CN | 104144463 A | 11/2014 |
| CN | 105868983 A | 8/2016 |
| EP | 2914047 A1 | 9/2015 |

OTHER PUBLICATIONS

CN103796203A, English Abstract and Translation.
CN104144463A, English Abstract and Translation.
1$^{st}$ Chinese Office Action, English Translation.
CN103441997A, English Abstract and U.S. Equivalent U.S. Pub. No. 2015/0119000.
CN105868983A, English Abstract and U.S. Equivalent U.S. Pub. No. 2017/0311160.
First Office Action for Chinese Application No. 201710726243.7, dated May 28, 2019, 7 Pages.

* cited by examiner

DATA ACCESS METHOD, USER EQUIPMENT AND SERVER

CROSS-REFERENCE TO RELATED APPLICATION

This application claims priority to Chinese Patent Application No. 201710726243.7 filed on Aug. 22, 2017, which is incorporated herein by reference in its entirety.

TECHNICAL FIELD

The present disclosure relates to the field of communication technology, in particular to a data access method, a User Equipment (UE), and a server.

BACKGROUND

Along with the rapid development of the Internet technology and the smart mobile devices, a medical worker working at a medical place has gradually begun to promote a mobile medical office system. For example, the medical worker may access medical data about a patient, e.g., medical images, through a handheld flat-panel device, or in the case that the medical worker is on a business trip or at a remote place, the medical worker may, using a mobile UE, view and access the medical data about the patient on the hospital Intranet through remote login or an application in time. Due to this mobile access mode, it is convenient for the medical worker to access the medical data, but a related security issue has become more and more serious.

In the related art, usually a wireless access mode is controlled using a password, i.e., the medical worker may remotely log in a central server system of a hospital through an account number and the password as authorization data.

However, with the advent of honeypot Wireless Fidelity (Wi-Fi) and pseudo base stations, it is very easy to sniff the account number and the password used during data transmission through data sniffing software. In addition, in the medical industry, the informatization construction is relatively weak for years, and it is very easy for any technical person who has a bad motive, e.g., hacker, to acquire the medical data about the patient through penetrating the central server system or creating a fake account number. The medical data about the patient belongs to a high-level personal privacy, so there is an urgent need in the medical industry to provide a method for remote and non-contact access to the central server system without any necessity to modify the structure of an information network significantly.

SUMMARY

A first object of the present disclosure is to provide a data access method. A second object of the present disclosure is to provide a further data access method. A third object of the present disclosure is to provide a UE (i.e., a terminal). A fourth object of the present disclosure is to provide a server. A fifth object of the present disclosure is to provide a data access system.

In a first aspect, the present disclosure provides in some embodiments a data access method, including steps of: acquiring, by a UE, authentication data from a first Near Field Communication (NFC) circuit; transmitting, by the UE, the authentication data to a second NFC circuit of a server for authentication via a network connection between the UE and the server; and in the case that the UE has been authenticated successfully, transmitting, by the UE, a data access request to the server via the network connection, and accessing to-be-accessed data that corresponds to the data access request and is transmitted by the server.

In a second aspect, the present disclosure provides in some embodiments a data access method, including steps of: receiving, by a server, first authentication data from a UE via a network connection, the first authentication data being acquired by the UE from a first NFC circuit of the UE itself; acquiring, by the server, second authentication data for authentication from a second NFC circuit of the server itself; comparing, by the server, the first authentication data with the second authentication data, and in the case that the first authentication data is identical to the second authentication data, determining that the UE has been authenticated successfully; and receiving, by the server, a data access request from the UE, acquiring to-be-accessed data corresponding to the data access request via the network connection, and allowing the UE to access the to-be-accessed data.

In a third aspect, the present disclosure provides in some embodiments a UE, including: an acquisition circuit configured to acquire authentication data from a first NFC circuit; a data transmission circuit configured to transmit the authentication data to a second NFC circuit of a server for authentication via a network connection between the UE and the server, and in the case that the UE has been authenticated successfully, transmit a data access request to the server via the network connection, and access to-be-accessed data that corresponds to the data access request and is transmitted by the server.

In a fourth aspect, the present disclosure provides in some embodiments a server, including: a data transmission circuit configured to receive first authentication data from a UE via a network connection, receive a data access request from the UE, acquire to-be-accessed data corresponding to the data access request, and allow the UE to access the to-be-accessed data via the network connection, the first authentication data being acquired by the UE from a first NFC circuit of the UE itself; an acquisition circuit configured to acquire second authentication data for authentication from a second NFC circuit of the server itself; and a processing circuit configured to compare the first authentication data with the second authentication data, and in the case that the first authentication data is identical to the second authentication data, determine that the UE has been authenticated successfully.

In a fifth aspect, the present disclosure provides in some embodiments a data access system, including the above-mentioned UE and the above-mentioned server.

The other aspects and advantages of the present disclosure will be given or may become apparent in the following description, or may be understood through the implementation of the present disclosure.

BRIEF DESCRIPTION OF THE DRAWINGS

In order to illustrate the technical solutions of the present disclosure in a clearer manner, the drawings desired for the present disclosure will be described hereinafter briefly. Obviously, the following drawings merely relate to some embodiments of the present disclosure, and based on these drawings, a person skilled in the art may obtain the other drawings without any creative effort.

DETAILED DESCRIPTION

In order to make the objects, the technical solutions and the advantages of the present disclosure more apparent, the present disclosure will be described hereinafter in a clear and complete manner in conjunction with the drawings and embodiments. Obviously, the following embodiments merely relate to a part of, rather than all of, the embodiments of the present disclosure, and based on these embodiments, a person skilled in the art may, without any creative effort, obtain the other embodiments, which also fall within the scope of the present disclosure.

In the following description, a UE is capable of accessing medical data stored in a server. Information system architecture adopted by different hospitals may be different from each other. To be specific, in Browser/Server (B/S) architecture, it is impossible for the UE to acquire the medical data from the server and store it locally. Instead, the UE may be connected to the server via a browser or the like, and after a relevant logic processing operation of the server, the server may present the medical data to the UE through the browser on the UE, so that a user of the UE may view the medical data. In Client/Server (C/S) architecture, the server may transmit the medical data corresponding to a data access request initiated by the UE to the UE via a network connection, and the UE may perform the relevant logic processing operation and then present the medical data to the user. In the embodiments of the present disclosure, the medical data in any one of the above architectures may be accessed.

The present disclosure will be described hereinafter in conjunction with the drawings and embodiments.

Currently, in order to provide a medical service conveniently, a medical worker may access to medical data about a patient, e.g., various medical images, through a handheld flat-panel device, or in the case that the medical worker is on a business trip or at a remote place, the medical worker may, using a mobile UE, view and access the medical data about the patient on the hospital Intranet through remote login or an application in time.

However, there is a security issue in the case that the medical worker remotely logs in a central server system of a hospital through an account number and a password as authorization data.

In the embodiments of the present disclosure, in view of the above, authentication data is stored in an NFC circuit and the UE is remotely authenticated via a network connection, so as to ensure the remote access security.

In the following, firstly a medical data access method at a UE side will be described.

Figure 1:
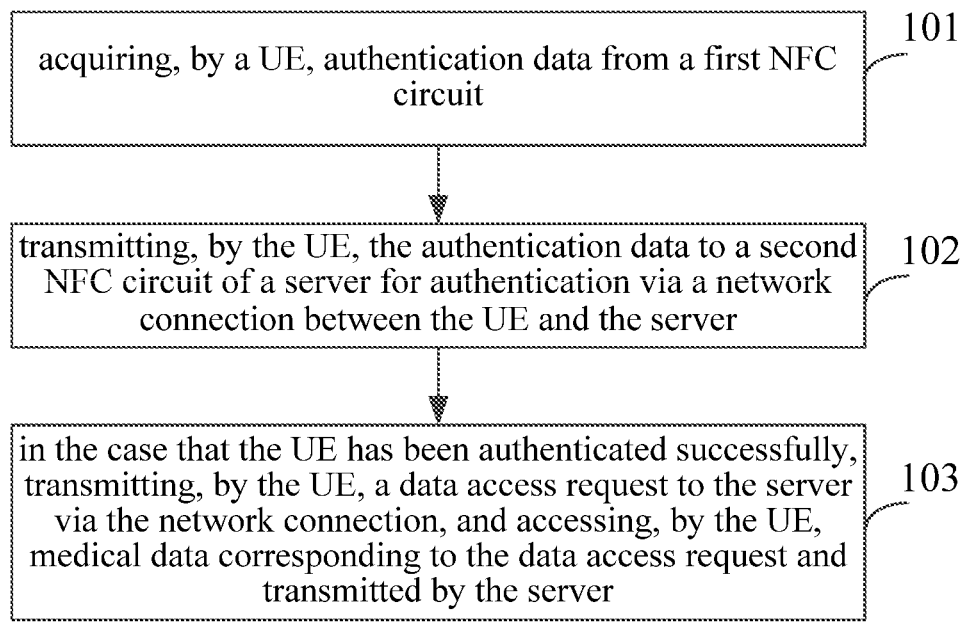
FIG. 1 is a flow chart of a medical data access method according to one embodiment of the present disclosure.

The present disclosure provides in some embodiments a medical data access method at a UE side which, as shown in FIG. 1, includes the following steps.

Step 101: acquiring, by a UE, authentication data from a first NFC circuit.

To be specific, in the embodiments of the present disclosure, the UE may be one or more of a flat-panel computer, a mobile phone, a smart wearable device, and the like.

In actual use, the UE may include the first NFC circuit, and the authentication data, e.g., account certificate information, may be stored in the first NFC circuit in accordance with the practical need.

In the case that the UE is connected to a server via a network connection and needs to be authenticated remotely, at first the UE may acquire the authentication data from the first NFC circuit in any one of various ways. To be specific, the UE may select the authentication data in accordance with the practical need, e.g., the UE may transmit an authentication data request to the first NFC circuit, and after the authentication data request is confirmed by the first NFC circuit, acquire the authentication data from the first NFC circuit. For another example, the UE may directly acquire the authentication data from the first NFC circuit.

Step 102: transmitting, by the UE, the authentication data to a second NFC circuit of the server for authentication via the network connection between the UE and the server.

To be specific, the UE may be connected to the server via a network connection, e.g., Wi-Fi or a $4^{th}$-Generation (4G) network connection. In a possible embodiment of the present disclosure, the UE may include a first communication circuit, and the server may include a second communication circuit. The first communication circuit and the second communication circuit may be connected to a Wireless Wide Area Network (WWAN) or Wireless Local Area Network (WLAN). Usually, the first communication circuit may be connected to the WLAN, while the second communication may be connected to the WWAN or WLAN.

Further, after the acquisition of the authentication data, the UE may transmit the authentication data to the second NFC circuit of the server for authentication via the network connection between the UE and the server.

It should be appreciated that, the server may be provided with the second NFC circuit which is mainly configured to validate the authentication data.

In order to further improve the security of the authentication data, in a possible embodiment of the present disclosure, the UE may encrypt the acquired authentication data, and then transmit the encrypted authentication data to the second NFC circuit via the network connection.

To be specific, the first NFC circuit may be provided with an encryption circuit (i.e., a security (SE) module in a NFC device). Through the encryption circuit, it is able to achieve hardware encryption on a security element of the first NFC circuit, or achieve software encryption using NFC Subscriber Identity Module (NFC-SIM) or Host Card Emulation (HCE). In a possible embodiment of the present disclosure, the authentication data stored in the NFC circuit may be encrypted through a random number generator of the encryption circuit using an encryption algorithm.

Step 103: in the case that the UE has been authenticated successfully, transmitting, by the UE, a data access request to the server via the network connection, and accessing to-be-accessed data that corresponds to the data access request and is transmitted by the server.

To be specific, in the case that the authentication data is validated by the second NFC circuit of the server, the UE may be authenticated successfully or unsuccessfully. It should be appreciated that, in the case that the UE has been authenticated successfully, the UE may transmit the data access request to the server via the network connection, and access the medical data that corresponds to the data access request and is transmitted by the server.

In a possible embodiment of the present disclosure, the UE may transmit the data access request to the server via the network connection, and then receive the medical data corresponding to the data access request. The data access request may include at least one first privilege label about a user corresponding to the UE. The medical data is data about a hospital department corresponding to the first privilege label, and the data is transmitted by the server in the case of determining the first privilege label is one of pre-stored privilege labels.

It should be appreciated that, the authentication data does not contain the privilege label, and instead, the first privilege label about the corresponding hospital department is transmitted each time the data is to be accessed. The first privilege label about the user is stored in the server. The first privilege label transmitted from the UE may be compared with that stored in the server, and in the case that the UE has been authenticated successfully, the UE may acquire the medical data from the corresponding hospital department.

To be specific, in actual use, different users have different access privileges. In order to further improve the access convenience and security of medical data, in a possible embodiment of the present disclosure, the authentication data may further include a privilege label about the user corresponding to the UE, so that the UE may directly notify the server of the privileges of each user. Doctors at different levels or at different departments may have different privileges.

To be specific, the authentication data containing a plurality of privilege labels is stored in a storage section of the first NFC circuit, and these privilege labels correspond to access privileges of a single medical worker on different sets of medical data in the hospital, such that the medical worker may access different sets of medical data with respective privileges. For example, a pharmacy worker may merely be allowed to, through his account, access the data about drug price, drug stock, and the like. At this time, it is merely necessary to configure a privilege label in the first NFC circuit for the pharmacy worker. For another example, a director of a medical department may be allowed to access the medical data from such departments as cardiology department and gastroenterology department. At this time, it is merely necessary to configure privilege labels corresponding to the respective sets of medical data in the first NFC circuit of the user.

It should be appreciated that, usually the NFC circuit has a data volume of 300K, and about 20 sets of authentication data containing the privilege labels about the users corresponding to the UE may be stored therein. By making full use of such hardware characteristics of the NFC circuit storing information being capable of being partitioned and labeled, it is able to dynamically adjust and control the different privileges of the medical workers at different levels to the medical data without any necessity to modify the structure of the existing hospital information system.

According to the medical data access method in the embodiments of the present disclosure, the UE acquires the authentication data from the first NFC circuit, transmits the authentication data to the second NFC circuit of the server for authentication via the network connection between the UE and the server, and in the case that the UE has been authenticated successfully, transmits the data access request to the server via the network connection, so as to access the medical data corresponding to the data access request and transmitted by the server. As a result, through the authentication data stored in the NFC circuit, it is able to remotely authenticate the UE via the network connection, thereby to improve the remote access convenience and security.

To be specific, before the UE acquires the authentication data from the first NFC circuit, the UE needs to create a network connection with the server. In a possible embodiment of the present disclosure, the data access method may further include: transmitting, by the UE, login information to the server, and in the case that the login information is validated successfully, creating the network connection with the server. The login information includes an account number and a password corresponding to the UE. In this way, it is able to further improve the data access security.

In order to further ensure the data access security and the privacy of the user data, the login information may further include information about a position where the UE is currently located.

Figure 2:
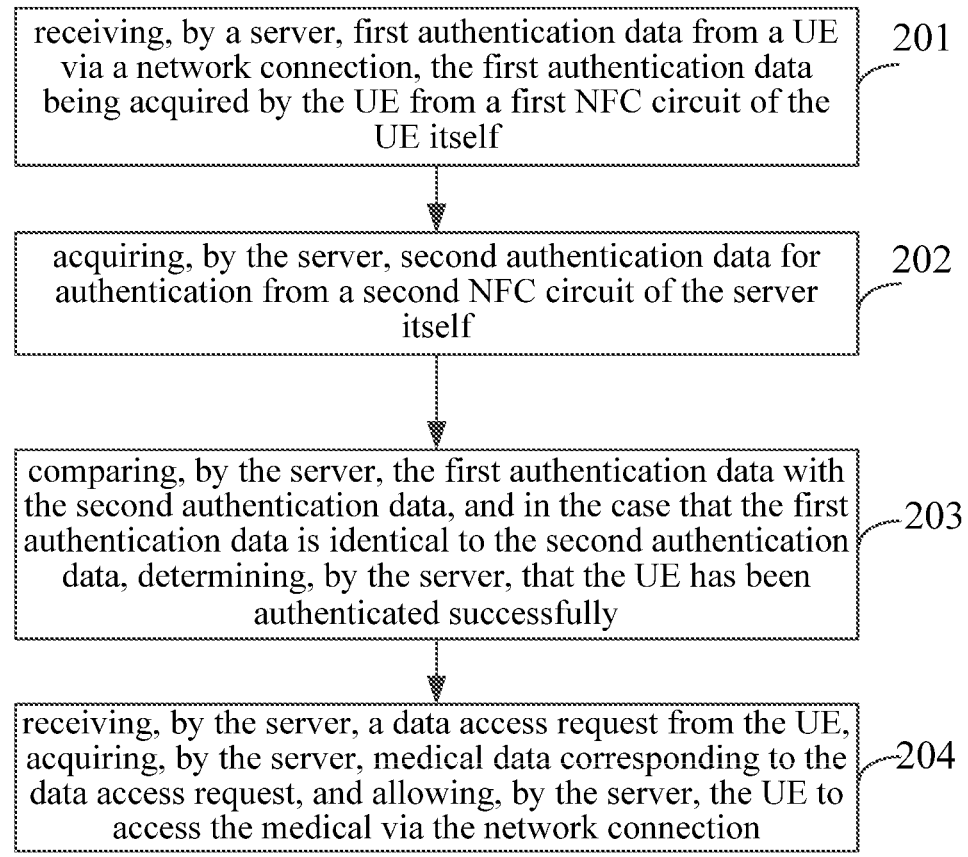
FIG. 2 is a flow chart of another medical data access method according to one embodiment of the present disclosure.

The present disclosure further provides in some embodiments a data access method at a server side which, as shown in FIG. 2, includes the following steps.

Step 201: receiving, by a server, first authentication data from a UE via a network connection, the first authentication data being acquired by the UE from a first NFC circuit of the UE itself.

Step 202: acquiring, by the server, second authentication data for authentication from a second NFC circuit of the server itself.

To be specific, after the creation of a network connection between the server and the UE, the server may receive the first authentication data from the UE. Upon the receipt of the first authentication data, the server may acquire the second authentication data for authentication from the second NFC circuit of the server itself, so as to validate the first authentication data.

Step 203: comparing, by the server, the first authentication data with the second authentication data, and in the case that the first authentication data is identical to the second authentication data, determining that the UE has been authenticated successfully.

Step 204: receiving, by the server, a data access request from the UE, acquiring the medical data corresponding to the data access request, and allowing the UE to access the medical data via the network connection.

To be specific, the server may compare the first authentication data with the second authentication data for the authentication. In the case that the first authentication data is identical to the second authentication data, the server may determine that the UE has been authenticated successfully, and in the case that the first authentication data is different from the second authentication data, the server may determine that the UE has been authenticated unsuccessfully.

In the case that the authentication data is encrypted, the server may decrypt the encrypted first authentication data, and then compare the decrypted first authentication data with the second authentication data.

It should be appreciated that, at least one group of medical data may be stored in the server, or the server may access to the at least one group of medical data.

To be specific, in the case that the authentication data is validated by the second NFC circuit of the server, the UE may be authenticated successfully or unsuccessfully. It should be appreciated that, in the case that the UE has been authenticated successfully, the server may receive the data access request from the UE, acquire the medical data corresponding to the data access request, and allow the UE to access the medical data via the network connection.

In a possible embodiment of the present disclosure, the server may receive the data access request via the network connection, and the data access request includes at least one first privilege label about the user corresponding to the UE. The server may acquire a second privilege label about the user from the second NFC circuit, determine whether the pre-stored second privilege label contains the first privilege label, determine that the user has a privilege to acquire the data from the hospital department corresponding to the first privilege label in the case that the second privilege label contains the first privilege label, and return the medical data to the UE via the network connection. The medical data is data from the hospital department.

To be specific, in actual use, different users have different access privileges. In order to further improve the access convenience and security of data, in a possible embodiment of the present disclosure, the first authentication data may further include a privilege label about the user corresponding to the UE, so that the UE may directly notify the server of the privileges of each user. Doctors at different levels or at different departments may have different privileges.

In this way, the server may receive the data access request via the network connection, and the data access request may include an identifier of the hospital department attempted to be accessed by the user corresponding to the UE. The server may determine whether the user corresponding to the UE has the privilege to access the hospital department in accordance with the privilege label in the first authentication data. In the case that the user has the privilege to access the hospital department, the server may acquire the medical data corresponding to the data access request.

According to the medical data access method in the embodiments of the present disclosure, the server receives the first authentication data from the UE via the network connection, acquires the second authentication data for authentication form the second NFC circuit of the server itself, compares the first authentication data with the second authentication data, and in the case that the first authentication data is identical to the second authentication data, determining that the authentication of the UE is successful. Then, the server receives the data access request from the UE, and acquires the medical data corresponding to the data access request, so as to allow the UE to access the medical data. As a result, through the authentication data stored in the NFC circuit, it is able to remotely authenticate the UE via the network connection, thereby to improve the remote access convenience and security.

To be specific, before the UE acquires the authentication data from the first NFC circuit, the UE needs to create a network connection with the server. In a possible embodiment of the present disclosure, the data access method may further include: the server receives login information from the UE, and in the case that the login information is validated successfully, creating the network connection with the UE. The login information includes an account number and a password corresponding to the UE.

In order to further ensure the medical data access security and the privacy of the user data, the login information may further include information about a position where the UE is currently located. In a possible embodiment of the present disclosure, the step of receiving, by the server, the login information from the UE and, in the case that the login information is validated successfully, creating the network connection with the UE includes: acquiring, by the server, a pre-stored secure position range; determining, by the server, whether the position where the UE is currently located is within the secure position range; and in the case that the position where the UE is currently located is within the secure position range, validating, by the server, the account number and the password in the login information, and after the account number and the password have been validated successfully, creating the network connection with the UE.

Through the above-mentioned way, it is able to prevent the occurrence any problem caused in the case that the user loses the UE outside a predetermined region. The server may be provided with a geofencing unit capable of being in communication with a communication unit of the UE and configured to determine whether the UE is located within a work place, so as to allow or not allow the server to create the network connection with the UE. For example, it should be appreciated that, even in the case that the user loses the UE outside the range of the hospital, it is almost impossible for a person who has picked up the UE or a thief to know the hospital corresponding to the UE and use the UE within the range of the hospital. At this time, the UE may probably be sold to the others. In this case, the geofencing unit may be configured to enable the UEs within a certain range of the hospital to access the server via the network connection, so as to prevent the lost UE to access the server illegally, thereby to further improve the data access security. The geofencing is a feature in a software program that uses, e.g., the Global Positioning System (GPS) or Radio Frequency Identification (RFID) to define geographical boundaries, and as a new application of a Location Based Service (LBS), it is used to define a virtual geographical boundary through a virtual fence. The UE is allowed to create the network connection with the server merely in the case that the UE enters a specific geographical range (e.g., the medical place) defined by the geofencing unit. The geofencing unit may be stored in the form of a software code in a computer-readable storage medium in the server, and for example, the software code is capable of being executed by a processor connected to the computer-readable storage medium so as to achieve the function of the geofencing unit.

Figure 3:
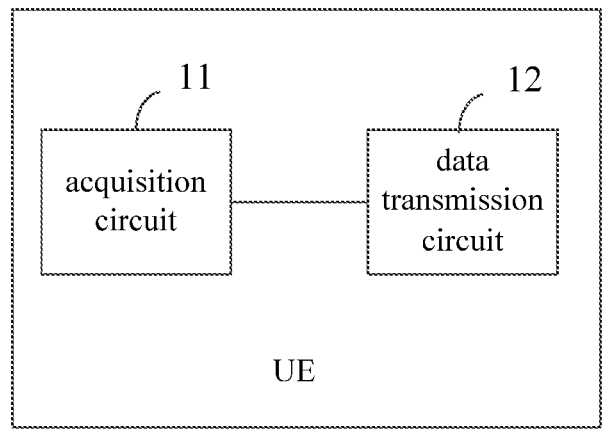
FIG. 3 is a block diagram of a UE according to one embodiment of the present disclosure.

The present disclosure further provides in some embodiments a UE which, as shown in FIG. 3, includes an acquisition circuit 11 and a data transmission circuit 12. The acquisition unit 11 is configured to acquire authentication data from a first NFC circuit. The data transmission circuit 12 is configured to transmit the authentication data to a second NFC circuit of a server for authentication via a network connection between the UE and the server, and in the case that the UE has been authenticated successfully, transmit a data access request to the server via the network connection, and access medical data corresponding to the data access request and transmitted by the server.

It should be appreciated that, the implementation of the UE may refer to that of the data access method mentioned hereinabove, and this will not be particularly defined herein.

According to the UE in the embodiments of the present disclosure, the UE acquires the authentication data from the first NFC circuit, transmits the authentication data to the second NFC circuit of the server for authentication via the network connection between the UE and the server, and in the case that the UE has been authenticated successfully, transmits the data access request to the server via the network connection, so as to access the medical data corresponding to the data access request in the server. As a result, through the authentication data stored in the NFC circuit, it is able to remotely authenticate the UE via the network connection, thereby to improve the remote access convenience and security.

Figure 4:
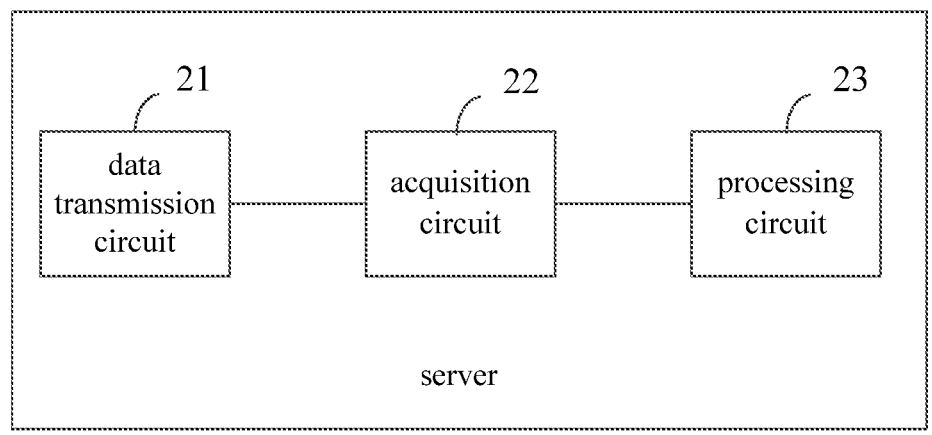
FIG. 4 is a block diagram of a server according to one embodiment of the present disclosure.

The present disclosure further provides in some embodiments a server which, as shown in FIG. 4, includes a data transmission circuit 21, an acquisition circuit 22 and a processing circuit 23. The data transmission circuit 21 is configured to receive first authentication data from the UE via a network connection, receive a data access request from the UE, acquire to-be-accessed data that corresponds to the data access request via the network connection, and allow the UE to access the to-be-accessed data. The first authentication data is acquired by the UE from a first NFC circuit of the UE itself. The acquisition circuit 22 is configured to acquire second authentication data for authentication from a second NFC circuit of the server itself. The processing circuit 23 is configured to compare the first authentication data with the second authentication data, and in the case that the first authentication data is identical to the second authentication data, determine that the UE has been authenticated successfully.

It should be appreciated that, the implementation of the server may refer to that of the data access method mentioned hereinabove, and this will not be particularly defined herein.

According to the server in the embodiments of the present disclosure, the server receives the first authentication data from the UE via the network connection, acquires the second authentication data for authentication from the second NFC circuit of the server itself, compares the first authentication data with the second authentication data, and in the case that the first authentication data is identical to the second authentication data, authenticate the UE successfully. Then, the server receives the data access request from the UE, and acquires the medical data corresponding to the data access request, so as to allow the UE to access the medical data via the network connection. As a result, through the authentication data stored in the NFC circuit, it is able to remotely authenticate the UE via the network connection, thereby to improve the remote access convenience and security.

Figure 5:
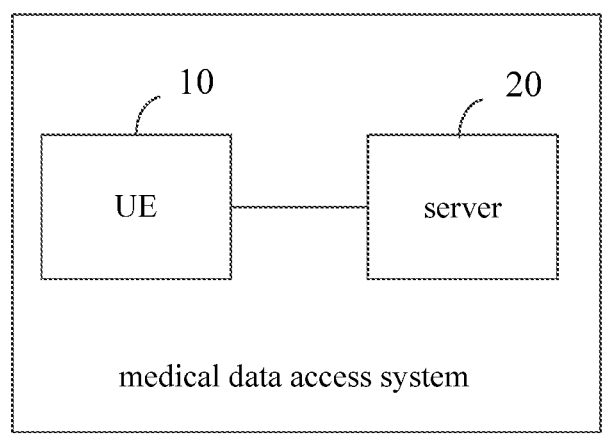
FIG. 5 is a block diagram of a medical data access system according to one embodiment of the present disclosure.

The present disclosure further provides in some embodiments a medical data access system which, as shown in FIG. 5, includes the above-mentioned UE 10 and the above-mentioned server 20.

It should be appreciated that, the implementation of the medical data access system may refer to that of the medical data access method mentioned hereinabove, and this will not be particularly defined herein.

The present disclosure provides in some embodiments a computer device, including a memory, a processor, and a computer program stored in the memory and capable of being executed by the processor. The computer program is executed by the processor, so as to implement the above-mentioned medical data access methods.

The present disclosure provides in some embodiments a nontransient computer-readable storage medium storing therein instructions. The instructions are capable of being executed by a processor, so as to implement the above-mentioned medical data access methods.

Such phrases as "one embodiment", "embodiments", "examples" and "for example" intend to indicate that the features, structures or materials are contained in at least one embodiment or example of the present disclosure, rather than referring to an identical embodiment or example. In addition, the features, structures, materials, or characteristics may be combined in any embodiment or embodiments in an appropriate manner. In the case of no conflict, the embodiments or examples or the features therein may be combined in any form.

In addition, such words as "first" and "second" are merely used to differentiate different components rather than to represent any order, number or importance, i.e., they are used to implicitly or explicitly indicate that there is at least one component. Further, such a phrase as "a plurality of" is used to indicate that there are at least two, e.g., two or three, components, unless otherwise specified.

Any process or method in the flow chart or described in any other manner may be understood as one or more modules, segments or parts containing one or more executable instructions for performing the steps, so as to achieve customized logical functions or processes. Apart from the described or discussed order, the steps may also be performed simultaneously or in a reverse order, so as to achieve the mentioned functions.

The logic and/or steps shown in the flow charts or described in any other manner may be a sequence of executable instructions for achieving the logical functions. The instructions may be stored in any computer-readable medium, and executed by a system, unit or device (e.g., a computer-based system, a system including a processor, or any other system capable of reading and executing the instruction from the system, unit or device), or a combination thereof. The computer-readable medium may be any unit capable of containing, storing, communicating, spreading or transferring a program which may be executed by the system, unit or device, or a combination thereof. The computer-readable medium may include, but not limited to, electrical connection member (electronic device) having one or more circuits, portable computer enclosure (magnetic unit), Random Access Memory (RAM), Read Only Memory (ROM), (Erasable Programmable ROM (EPROM), flash memory, optical fiber unit, and Compact Disc ROM (CDROM). In addition, the computer-readable medium may also be paper onto which the program is printed or any other appropriate medium. The paper or the other appropriate medium may be optically scanned, compiled, interpreted or treated in any other appropriate manner, so as to acquire the program and store it in a memory.

It should be appreciated that, the embodiments of the present disclosure may be implemented through hardware, software, firmware, or a combination thereof. The steps or methods may be implemented by the software or firmware stored in the memory and executed by an appropriate system. In the case that the hardware is adopted, the steps or methods may be implemented by a discrete logic circuit having a logic gate circuit capable of processing a data signal, an application-specific integrated circuit (ASIC) having an appropriate combinational logic gate circuits, a programmable gate array (PGA), or a field programmable gate array (FPGA), or a combination thereof.

It should be further appreciated that, all or parts of the steps in the method may be implemented by related hardware using a program stored in a computer-readable storage medium. The program is executed so as to perform a step or a combination of the steps.

In addition, the functional units in the embodiments of the present disclosure may be integrated into a processing module, or the functional units may exist independently, or two or more functional units may be combined together. The functional units may be implemented in the form of hardware or software. In the case that the functional units are implemented in the form of software and sold or used as a separate product, they may also be stored in the computer-readable storage medium. The storage medium may be ROM, magnetic disc or optical disc.

The above are merely the preferred embodiments of the present disclosure, but the present disclosure is not limited thereto. Obviously, a person skilled in the art may make further modifications and improvements without departing from the spirit of the present disclosure, and these modifications and improvements shall also fall within the scope of the present disclosure.

What is claimed is:

1. A data access method, comprising:
   acquiring, by a User Equipment (UE), authentication data from a first Near Field Communication (NFC) circuit;
   transmitting, by the UE, the authentication data to a second NFC circuit of a server for authentication via a network connection between the UE and the server; and
   in the case that the UE has been authenticated successfully, transmitting, by the UE, a data access request to the server via the network connection, and accessing, by the UE, to-be-accessed data that corresponds to the data access request and is transmitted by the server,
   wherein the authentication data comprises a privilege label about a user corresponding to the UE,
   wherein the step of, in the case that the UE has been authenticated successfully, transmitting, by the UE, the data access request to the server via the network connection and accessing, by the UE, the to-be-accessed data that corresponds to the data access request and is transmitted by the server comprises:
      in the case that the UE has been authenticated successfully, transmitting the data access request to the server, wherein the data access request comprises at least one identifier of a type of data attempted to be accessed by the user corresponding to the UE; and
      accessing, by the UE, the to-be-accessed data returned from the server via the network connection, wherein the to-be-accessed data is allowed to be accessed after the server has determined that the user has a privilege to access a type of the data.

2. The data access method according to claim 1, wherein the to-be-accessed data is medical data, and the type of the data is a type of a hospital department.

3. The data access method according to claim 1, wherein the step of, in the case that the UE has been authenticated successfully, transmitting, by the UE, the data access request to the server via the network connection and accessing the to-be-accessed data that corresponds to the data access request and is transmitted by the server comprises:
   transmitting, by the UE, the data access request to the server via the network connection, wherein the data access request comprises at least one first privilege label about a user corresponding to the UE; and
   accessing, by the UE, the to-be-accessed data corresponding to the data access request, wherein the to-be-accessed data is data of a type corresponding to the first privilege label, and the data is transmitted by the server after the server has determined that the first privilege label is one of pre-stored privilege labels.

4. A data access method, comprising:
   receiving, by a server, first authentication data from a User Equipment (UE) via a network connection, wherein the first authentication data is acquired by the UE from a first Near Field Communication (NFC) circuit of the UE;
   acquiring, by the server, second authentication data for authentication from a second NFC circuit of the server;
   comparing, by the server, the first authentication data with the second authentication data, and in the case that the first authentication data is identical to the second authentication data, determining, by the server, that the UE has been authenticated successfully; and
   receiving, by the server, a data access request from the UE, acquiring, by the server, to-be-accessed data corresponding to the data access request, and allowing, by the server, the UE to access the to-be-accessed data via the network connection,
   wherein the first authentication data comprises a privilege label about a user corresponding to the UE,
   wherein the step of receiving, by the server, the data access request from the UE, acquiring, by the server, the to-be-accessed data corresponding to the data access request, and allowing, by the server, the UE to access the to-be-accessed data via the network connection comprises:
      receiving, by the server, the data access request via the network connection, wherein the data access request comprises an identifier of a type of data attempted to be accessed by the user corresponding to the UE;
      determining, by the server, whether the user corresponding to the UE has a privilege to access the type of the data in accordance with the privilege label in the first authentication data; and
      in the case of determining that the user has the privilege to access the type of the data, acquiring, by the server, the to-be-accessed data that corresponds to the data access request.

5. The data access method according to claim 4, wherein the to-be-accessed data is medical data, and the type of the data is a type of a hospital department.

6. The data access method according to claim 4, wherein the step of receiving, by the server, the data access request from the UE, acquiring, by the server, the to-be-accessed data corresponding to the data access request, and allowing, by the server, the UE to access the to-be-accessed data via the network connection comprises:
   receiving, by the server, the data access request via the network connection, wherein the data access request comprises at least one first privilege label about a user corresponding to the UE;
   acquiring, by the server, a pre-stored second privilege label about the user from the second NFC circuit, and determining, by the server, whether the pre-stored second privilege label contains the first privilege label; and
   in the case of determining that the pre-stored second privilege label contains the first privilege label, determining, by the server, that the user has a privilege to acquire data of the type corresponding to the first privilege label, and allowing, by the server, the UE to access the to-be-accessed data via the network connection, wherein the to-be-accessed data is the data of the type corresponding to the first privilege label.

7. The data access method according to claim 4, wherein prior to the step of receiving, by the server, the first authentication data from the UE via the network connection, the data access method further comprises:
   receiving, by the server, login information from the UE, and in the case that the login information is validated successfully, creating, by the server, the network connection with the UE, wherein the login information comprises an account number and a password corresponding to the UE.

8. The data access method according to claim 7, wherein the login information further comprises information about a position where the UE is currently located,
   wherein the step of receiving, by the server, the login information from the UE and, in the case that the login information is validated successfully, creating the network connection with the UE comprises:
      acquiring, by the server, a pre-stored secure position range;

determining, by the server, whether the information about the position where the UE is currently located is within the secure position range; and in the case of determining that the information about the position where the UE is currently located is within the secure position range, validating, by the server, the account number and the password in the login information, and after the account number and the password have been validated successfully, creating, by the server, the network connection with the UE.

9. A User Equipment (UE), comprising:

an acquisition circuit configured to acquire authentication data from a first Near Field Communication (NFC) circuit; and a data transmission circuit configured to transmit the authentication data to a second NFC circuit of a server for authentication via a network connection between the UE and the server, and in the case that the UE has been authenticated successfully, transmit a data access request to the server via the network connection, and access to-be-accessed data that corresponds to the data access request and is transmitted by the server, wherein the authentication data comprises a privilege label about a user corresponding to the UE, wherein the data transmission circuit is further configured to:

in the case that the UE has been authenticated successfully, transmit the data access request to the server, wherein the data access request comprises at least one identifier of a type of data attempted to be accessed by the user corresponding to the UE, and access the to-be-accessed data returned from the server via the network connection, wherein the to-be-accessed data is allowed to be accessed after the server has determined that the user has a privilege to access a type of the data.

10. The UE according to claim 9, wherein the to-be-accessed data is medical data, and the type of the data is a type of a hospital department.

11. The UE according to claim 9, wherein the data transmission circuit is further configured to:

transmit the data access request to the server via the network connection, wherein the data access request comprises at least one first privilege label about a user corresponding to the UE; and access the to-be-accessed data corresponding to the data access request, wherein the to-be-accessed data is data of a type corresponding to the first privilege label, and the data is transmitted by the server after the server has determined that the first privilege label is one of pre-stored privilege labels.

12. A server configured to be connected to the UE according to claim 9 via a network connection, wherein the server comprises:

a data transmission circuit configured to receive first authentication data from the UE via a network connection, receive a data access request from the UE, acquire to-be-accessed data corresponding to the data access request, and allow the UE to access the to-be-accessed data via the network connection, wherein the first authentication data is acquired by the UE from a first Near Field Communication (NFC) circuit of the UE;

an acquisition circuit configured to acquire second authentication data for authentication from a second NFC circuit of the server; and a processing circuit configured to compare the first authentication data with the second authentication data, and in the case that the first authentication data is identical to the second authentication data, determine that the UE has been authenticated successfully.

13. The server according to claim 12, wherein the to-be-accessed data is medical data, and the type of the data is a type of a hospital department.

14. The server according to claim 12, wherein the data transmission circuit is further configured to:

receive the data access request via the network connection, wherein the data access request comprises at least one first privilege label about a user corresponding to the UE;

acquire a pre-stored second privilege label about the user from the second NFC circuit, and determine whether the pre-stored second privilege label contains the first privilege label; and in the case of determining the pre-stored second privilege label contains the first privilege label, determine that the user has a privilege to acquire data of the type corresponding to the first privilege label, and allow the UE to access the to-be-accessed data via the network connection, wherein the to-be-accessed data is the data of the type corresponding to the first privilege label.

15. The server according to claim 12, wherein the data transmission circuit is further configured to: prior to the reception of the first authentication data from the UE via the network connection, receive login information from the UE, and in the case that the login information is validated successfully, create the network connection with the UE, wherein the login information comprises an account number and a password corresponding to the UE.

16. The server according to claim 15, wherein the login information further comprises information about a position where the UE is currently located, wherein the data transmission circuit is further configured to:

acquire a pre-stored secure position range;

determine whether the information about the position where the UE is currently located is within the secure position range; and in the case that the information about the position where the UE is currently located is within the secure position range, validate the account number and the password in the login information, and after the account number and the password have been validated successfully, create the network connection with the UE.

* * * * *